(12) United States Patent
Gately

(10) Patent No.: US 6,180,810 B1
(45) Date of Patent: Jan. 30, 2001

(54) SILYL AMINES

(75) Inventor: Daniel A. Gately, Sugar City, CO (US)

(73) Assignee: Boulder Scientific Company, Mead, CO (US)

( * ) Notice: Under 35 U.S.C. 154(b), the term of this patent shall be extended for 0 days.

(21) Appl. No.: 09/444,503

(22) Filed: Nov. 22, 1999

Related U.S. Application Data

(63) Continuation-in-part of application No. 09/016,641, filed on Jan. 30, 1998.

(51) Int. Cl.[7] ....................................................... C07F 7/10
(52) U.S. Cl. ............................................ 556/410; 556/428
(58) Field of Search ..................................... 556/410, 427, 556/428

(56) References Cited

PUBLICATIONS

CA:121:84125 abs of Helv Chim Acta by Uhlig 77(4) pp 972–80, 1994.*
CA:121:58130 abs of Chem Ber by Uhlig 127(6) pp 985–90, 1994.*
CA:120:298764 abs of J Organomet Chem by Uhlig 463 (1–2) pp 73–6, 1993.*
CA:120:298681 abs of J Organmet Chem by Uhlig 467(1) pp 31–5, 1994.*

* cited by examiner

*Primary Examiner*—Jean F Vollano
(74) *Attorney, Agent, or Firm*—Edward S. Irons

(57) ABSTRACT

Silyl amine compounds which have a proton available for covalent bonding to a metallocene metal center are disclosed.

3 Claims, No Drawings

SILYL AMINES

This application is a continuation-in-part of application Ser. No. 09/016,641 filed Jan. 30, 1998.

FIELD OF THE INVENTION

This invention relates to silyl amine compounds. More particularly, the invention relates to silyl amines which bond covalently to a metal center of a complex to provide an olefin polymerization catalyst component.

BACKGROUND OF THE INVENTION

Olefin polymerization catalyst or catalyst components comprising geometry metal complexes having a silyl amine moiety bound to the metal center preparation are described in the prior art. See, e.g., WO 98/49212 (references cited at page 1, lines 6–15). Typical syntheses of such complexes entail treatment of a lithiated ligand precursor with $Cl_2Si(CH_3)_2$. See, e.g., WO 98/27103 (Example 5c). Disadvantages of these procedures include a requirement for excess $Cl_2Si(CH_3)_2$ and the production of undesirable by-products with consequent need for expensive purification procedures.

Certain silyl triflates and amino substituted silyl triflates are reported to show reactivity towards nucleophiles and, hence, to constitute useful silylating reagents and transmitters of amino silyl groups. Uhlig, et al. (1994) *J. Organometallic Chem.* 467(1):31–35. Diisopropyl and diisobutyl ditriflates are described in Corey (1990) *Tetrahedron Letters* 31(5):601–604.

Mesylates of the formula $(CH_3SO_3)_2$-Si(t-Bu)$_2$ are described in Matyjaszewski (1998) *J. Organometallic Chem.* 340:7–12.

U.S. Pat. No. 4,939,250 describes trifluoromethane sulfonic (triflate) and 1,1,2,2-tetrafluoro ethane sulfonate used β-lactam silylating agents.

However, the prior art is not known to describe any silyl amine compound which forms a covalent bond with the metal center of any complex.

SUMMARY OF THE INVENTION

The invention provides novel silyl amine compounds which may covalently add directly to the metal center of a metallocene. The silyl amine compounds of this invention have the generic Formula I:

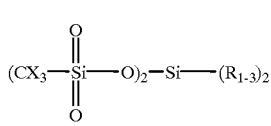

(I)

in which X is H or F; $R_1$, $R_2$, $R_3$=alkyl or aryl or a combination of alkyl or aryl; $R_4$=H.

In preferred embodiments of the invention, $R_1$, $R_2$ and $R_3$ are the same or different $C_1$ or $C_{10}$ alkyl groups, most preferably methyl. Specific preferred embodiments of the invention are:

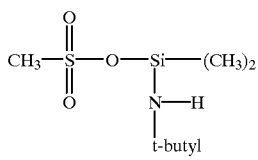

and

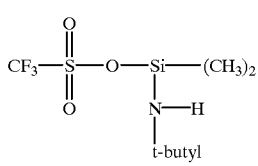

The invention also includes methods for the synthesis of Formula I silyl amines.

Pursuant to one synthesis method, a compound of Formula IV

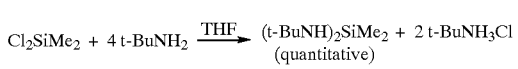

is treated with an amine of formula $(R_{1-3})NH_2Si(R_{1-3})_2^3$, wherein X and $R_1$, $R_2$ and $R_3$ are as described.

EXAMPLE 1

Preparation of a Formula (II) Silane (a) Preparation of $(t-BuNH)_2SiMe_2$

A 12 L flask equipped with an addition funnel and reflux condenser was charged with $t-BuNH_2$ (11 mol, 805 g) and THF (7 L). The solution was slowly treated with $Cl_2SiMe_2$ (5 mol, 645 g). An exothermic reaction ensued. After the pot temperature had dropped to 40° C., the white slurry reaction mixture containing $t-BuNH_3Cl$ was filtered, and the cake was washed with THF (1 L). The filtrate was reduced to an oil that contained 97% pure $(t-BuNH)_2SiMe2$ ($^1H$ NMR). Yield was quantitative (1 Kg). See equation (1).

$$Cl_2SiMe_2 + 4\,t\text{-}BuNH_2 \xrightarrow{THF} (t\text{-}BuNH)_2SiMe_2 + 2\,t\text{-}BuNH_3Cl \quad \text{(quantitative)} \tag{1}$$

(b) Preparation of 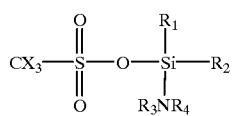

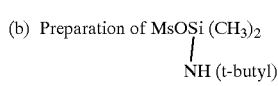

The $(t-BuNH)_2SiMe_2$ prepared as described in Example 1(a) was added to one equivalent of neat $(MsO)_2SiMe_2.0.5HCl$ at room temperature, resulting in a 50–60° C. exotherm. The resulting oil which contained insoluble solids was filtered through a glass frit. The cake was >98% pure $(t-BuNH)(MsO)SiMe_2$ ($^1NMR$). See equation (2).

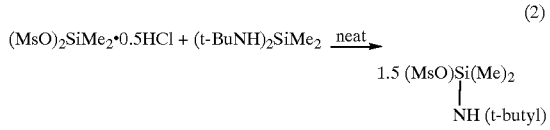

(2)

EXAMPLE 2

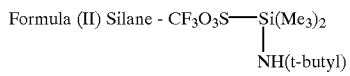

was prepared as described in Example 1 (Equation 2) except that (TfO)$_2$Si(Me)2 replaces (MsO)$_2$SiMe$_2$.0.5 HCl.

EXAMPLE 3

Preparation of 2-Methylcyclopentadienyl(t-Butylamido) Dimethylsilane (Equation 3)

A 1 L flask was charged with 2-methylcyclopentadiene (16 g, 200 mmol) and THF (160 g). The solution was cooled (−10° C.) and treated with n-BuLi (1.6 M, 125 mL, 200 mmol). After the resulting white heterogeneous solution was stirred at room temperature for thirty minutes, the solution was treated with (t-BuNH) (MsO)SiMe$_2$ (47 g, 190 mmol) present in the Example 2 reaction mixture, and the solution was stirred overnight. The solution was filtered through Celite, the residual LiOMs was washed with ether (500 mL), and the filtrate was reduced to an oil. No further purification was necessary. Yield was quantitative. See equation (3):

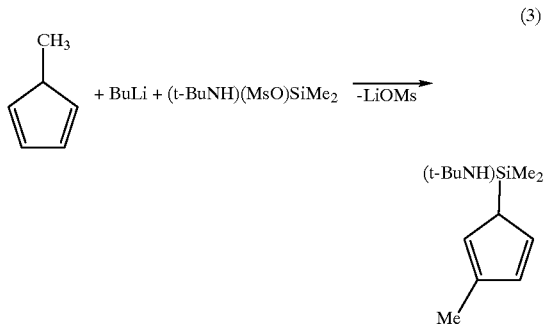

(3)

In this example, 2-methylcyclopentadiene may be replaced by cyclopentadiene to provide a quantitative yield of cyclopentadienyl (t-butyl amido) dimethylsilane.

Likewise, 2-methylcyclopentadiene may be replaced by 3-methyl-2-ethyl-cyclopentadiene to provide a quantitative yield of 3-methyl-2-ethyl-cyclopentadienyl (t-butyl amido) dimethylsilane, or t-BuNH(TfO)Si(Me)$_2$ may be used with similar results.

This example illustrates a method in which the silane is added directly to the reaction mixture in which an alkali metallide is formed. Alternatively, the alkali metallide, here lithium-2-methylcyclopentadiene, may be isolated from the reaction mixture in known manner and thereafter reacted with the silane.

EXAMPLE 4

Preparation of 2-Methylindenyl(t-Butylamido) Dimethylsilane (Equation 4)

A 5 L flask was charged with 2-methylindene (1.67 mol, 217 g) and ether (1.5 L). The solution was cooled (−10° C.) and treated with BuLi (1.67 mol, 1.04 L). After the solution was stirred for one hour at room temperature, the solution was cooled (−10° C.) and Me$_2$Si(MsO)NH(t-Bu) produced in the manner described in Example 1 was added in one portion, resulting in a 20° C. exotherm. After one hour at room temperature, the solution was filtered through Celite, the residual solid LiOMs was washed with ether (1.5 L), and the filtrate was reduced to a yellow oil that contained >98% pure 2-methylindenyl(t-butylamido) dimethylsilane ($^1$H NMR) in quantitative yield. See equation (4):

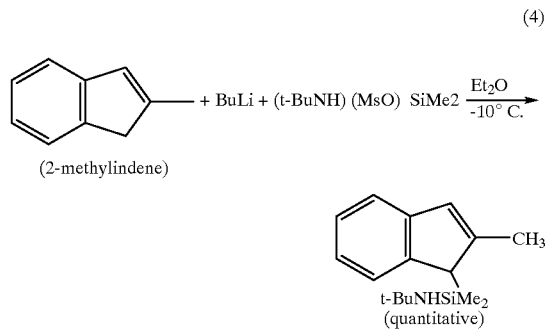

(4)

In this example, t-BuNH(TfO)Si(Me)$_2$ may be used instead of t-BuNH(MsO)Si(Me)$_2$, 2-methylindene may be replaced with fluorene to provide a quantitative yield of 9-fluorenyl-t-butylamido dimethylsilane, and 2-methylindene may be replaced with bromobenzene to obtain a quantitative yield of the expected phenyl-t-butylamido dimethylsilane.

EXAMPLE 5

Preparation of bis(2-methyl-4,5-benzoindenyl) dimethylsilane (equation 5)

A 2L flask charged with 2-methyl-4,5-benzo(indene) (73 g, 405 mmol) and ether (500 mL) was cooled to −10° C. and treated with n-BuLi (1.6 M, 255 mL, 405 mmol). The solution was allowed to warm to room temperature for 30 minutes, cooled to about −10° C., and then treated with a neat Formula I silane (MsO)$_2$SiMe$_2$-0.5 HCl (54g, 203 mmol) resulting in a 10–15° C. exotherm. After one hour at room temperature, the white slurry was treated with CH$_2$Cl$_2$ (500 mL), and the solution was filtered through Celite into a 5L flask. The solids were washed with CH$_2$Cl$_2$ (500 mL), and the filtrate was evacuated to dryness. The white solid residue was treated with ether (200 mL), and the solvent was evacuated so that most of the residual CH$_2$Cl$_2$ was removed. The solid was then treated with ether (1 L) and triturated for thirty minutes before filtering and washing the white solid with ether (200 mL). Yield: 20–50%. The 2-methyl-4,5-benzo(indene) was recovered by treatment of the filtrate with NaOH (20 wt %) in THF. See equation (5).

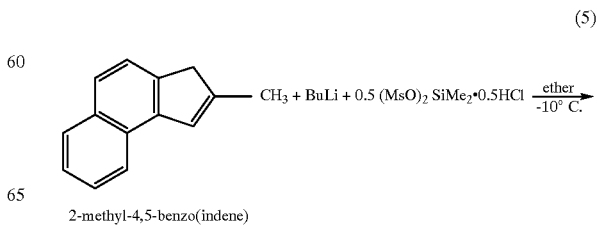

(5)

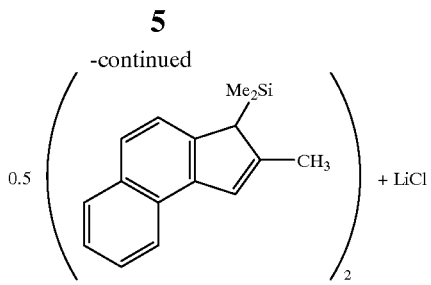

EXAMPLE 5(a)

The above procedure was repeated, except that (MSO)$_2$SiMe$_2$.0.5HCl was replaced with (TfO)$_2$Si(Me)$_2$. The yield of bis(2-methyl-4,5-benzoindenyl) dimethylsilane was 60–65%.

EXAMPLE 6

Preparation of Metallocene Catalyst from the Example 5 Product (Equation 6)

A 1 L flask was charged with bis(2-methyl-4,5-benzoindenyl) dimethylsilane (48 g, 115 m mol), toluene (480 mL), and ether (20 g, 270 mmol). The solution was cooled (–10° C.) and then treated with BuLi (1.6 M, 145 mL, 230 mmol). After the tanned-colored heterogeneous solution was stirred at room temperature for two hours, the solution was cooled (–20° C.) and treated with ZrCl$_4$ (27 g, 115 mmol). By the time the solution had warmed to –10° C., a bright yellow solution had resulted. After the yellow solution was stirred at room temperature for 2 hours, the solution was filtered, and the yellow solid was washed with toluene until the filtrate was pale yellow. The yellow filter cake was treated with an equal mass of Celite, the solids were slurried in dry CH$_2$Cl$_2$, and the product was extracted with CH$_2$Cl$_2$ through a layer of Celite into a 12 L flask that contained toluene (1 L); the extraction was stopped when the yellow color of the filtrate had turned translucent. The CH$_2$Cl$_2$ solvent was evaporated to give a toluene-slurry of yellow crystals. The solution was filtered, the yellow crystals were washed with toluene (1 L), and the yellow solid was slurried in toluene (5 L) for four hours. The solution was filtered to give 28 grams of diastereomerically pure metallocene ($^1$H NMR; yield—38%). See equation (6).

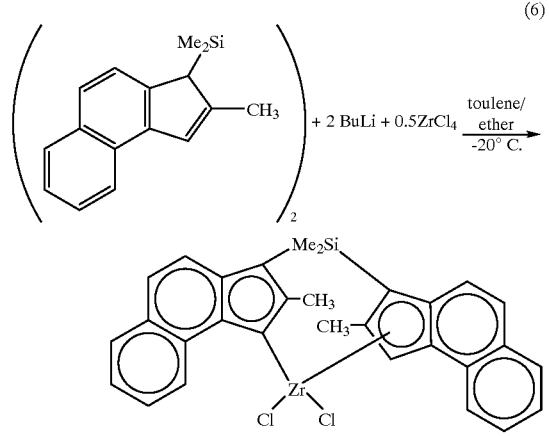

EXAMPLE 7

Preparation of Bis(3-Trimethylsilyl (TMS) indenyl) ethane (Equation 7)

A 1L flask was charged with ethylene bis-indene (EBI) (0.100 mol, 26g) and THF (260g). The solution was cooled (–10° C.) and treated with BuLi (0.200 mol. 125 mL). After one hour at RT, the solution was cooled (–10° C.) and treated with Me$_3$Si(OMS) (0.200 mol., 34 g) in one portion. After thirty minutes at RT, the solution was filtered through Celite, the solids containing rac/meso bis(TMS) EBI were washed with THF (130 g), and the filtrate was reduced giving a solid that contained 98% rac-meso product in >98% yield. The product was extracted with heptane to separate the rac and meso isomers.

This procedure is illustrated by the following equation (7):

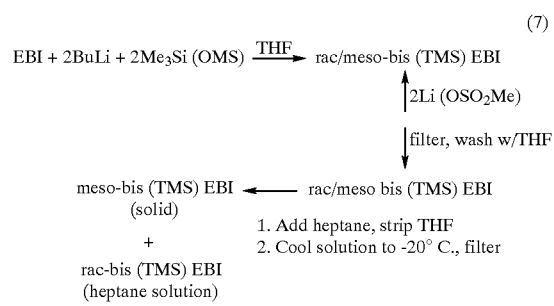

The above procedure was repeated with the EBI analogs bis(2-methylindenyl) ethane, bis(4,7-dimethylindenyl) ethane, cyclopentadiene and methylcyclopentadiene with similar results.

I claim:

1. A compound of Formula I:

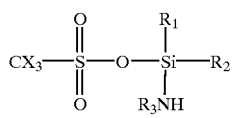

in which X is H or F and R$_1$, R$_2$, R$_3$ is alkyl or aryl.

2. A compound having the formula:

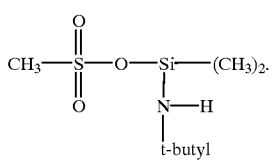

3. The compound having the formula:

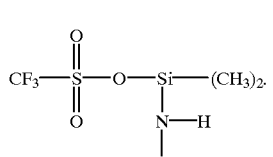

* * * * *

UNITED STATES PATENT AND TRADEMARK OFFICE
CERTIFICATE OF CORRECTION

PATENT NO. : 6,180,810 B1
DATED : January 30, 2001
INVENTOR(S) : Daniel A. Gately Page 1 of 1

It is certified that error appears in the above-identified patent and that said Letters Patent is hereby corrected as shown below:

Column 2,
Line 66, delete "cake" and insert -- oil --.

Column 4,
Line 44, delete "Formula I".

Signed and Sealed this

Sixteenth Day of April, 2002

Attest:

JAMES E. ROGAN
Attesting Officer     Director of the United States Patent and Trademark Office